United States Patent [19]
Lundgren et al.

[11] Patent Number: 5,863,903
[45] Date of Patent: Jan. 26, 1999

[54] USE OF HYDROXY ALKYL PIPERIDINE AND PYRROLIDINE COMPOUNDS TO TREAT DIABETES

[75] Inventors: Karsten Lundgren, Frederiksberg; Ole Kirk, Virum, both of Denmark

[73] Assignee: Novo Nordisk A/S, Bagsvaerd, Denmark

[21] Appl. No.: 404,077

[22] Filed: Mar. 14, 1995

Related U.S. Application Data

[63] Continuation-in-part of Ser. No. 209,654, Mar. 10, 1994, abandoned.

[30] Foreign Application Priority Data

Mar. 9, 1994 [DK] Denmark ................................ 0277/94

[51] Int. Cl.$^6$ ...................... C07D 211/36; C07D 207/10; A01N 43/04; C07H 19/00
[52] U.S. Cl. ............................ 514/43; 514/315; 514/317; 514/423; 514/424; 514/426; 514/428; 514/866; 536/28.1; 536/28.6; 546/229; 546/232; 546/233; 546/235; 546/236; 546/237; 546/238; 546/240; 546/243; 546/244; 546/246; 546/247; 546/242; 546/248; 548/542; 548/544; 548/557; 548/500; 548/567; 548/571; 548/572; 548/573
[58] Field of Search ..................................... 546/242, 248, 546/236, 229, 232, 233, 235, 237, 238, 240, 243, 244, 246, 247; 548/574, 556, 544, 571, 572, 573, 542, 557, 560, 567; 536/28.1, 28.6; 514/43, 315, 317, 425, 428, 866, 424, 423, 426

[56] References Cited

U.S. PATENT DOCUMENTS 5,276,120  1/1994  Wong et al. .............................. 546/242

FOREIGN PATENT DOCUMENTS

| 0 000 947 | 3/1979 | European Pat. Off. . |
| 0 022 192 | 1/1981 | European Pat. Off. . |
| 0 375 651 | 6/1990 | European Pat. Off. . |
| 0 481 950 | 4/1992 | European Pat. Off. . |
| 0 528 495 | 2/1993 | European Pat. Off. . |
| 88-125070 | 5/1988 | Japan ...................................... 546/242 |
| 92/21657 | 12/1992 | WIPO .................................... 546/242 |

OTHER PUBLICATIONS

Chemical abstract vol. 123, No. 257,141, Jespersen et al, 1994, "Isofagomin, an effective new glycosidao inhibitor".

*Primary Examiner*—John Kight
*Assistant Examiner*—Raymond Covington
*Attorney, Agent, or Firm*—Steve T. Zelson; Cheryl H. Agris; Carol E. Rozek

[57] ABSTRACT

The present invention relates to hydroxy alkyl piperidine compounds and pharmaceutical compositions thereof which can be used to treat diabetes.

8 Claims, No Drawings

USE OF HYDROXY ALKYL PIPERIDINE AND PYRROLIDINE COMPOUNDS TO TREAT DIABETES

CROSS-REFERENCE TO RELATED APPLICATIONS

This is a continuation-in-part of application Ser. No. 08/209,654 filed on Mar. 10, 1994, now abandoned, which is incorporated herein by reference.

FIELD OF THIS INVENTION

The present invention relates to novel compounds, the use of these compounds as medicament, the use of these medicaments in the treatment of diabetes and pharmaceutical compositions containing these compounds.

BACKGROUND OF THIS INVENTION

Diabetes is characterized by an impaired glucose metabolism manifesting itself among other things by an elevated blood glucose level in the diabetic patients. Underlying defects lead to a classification of diabetes into two major groups: type 1 diabetes, or insulin demanding diabetes mellitus (IDDM), which arises when patients lack β-cells producing insulin in their pancreatic glands, and type 2 diabetes, or non-insulin dependent diabetes mellitus (NIDDM), which occurs in patients with an impaired β-cell function besides a range of other abnormalities.

Type 1 diabetic patients are currently treated with insulin, while the majority of type 2 diabetic patients are treated either with sulfonylureas that stimulate β-cell function or with agents that enhance the tissue sensitivity of the patients towards insulin or with insulin. Among the agents applied to enhance tissue sensitivity towards insulin, metformin is a representative example.

Even though sulfonylureas are widely used in the treatment of NIDDM, this therapy is, in most instances, not satisfactory: In a large number of NIDDM patients, sulfonylureas do not suffice to normalize blood sugar levels and the patients are, therefore, at high risk for acquiring diabetic complications. Also, many patients gradually lose the ability to respond to treatment with sulfonylureas and are thus gradually forced into insulin treatment. This shift of patients from oral hypoglycaemic agents to insulin therapy is usually ascribed to exhaustion of the β-cells in NIDDM patients.

In normals as well as in diabetics, the liver produces glucose in order to avoid hypoglycemia. This glucose production is derived either from the release of glucose from glycogen stores or from gluconeogenesis, which is a de novo intracellular synthesis of glucose. In type 2 diabetes, however, the regulation of hepatic glucose output is poorly controlled and is increased, and may be doubled after an overnight fast. Moreover, in these patients there exists a strong correlation between the increased fasting plasma glucose levels and the rate of hepatic glucose production (reviewed in R. A. De Fronzo: *Diabetes* 37 (1988), 667–687; A. Consoli: *Diabetes Care* 15 (1992), 430–441; and J. E. Gerich: *Horm.Metab.Res.* 26 (1992), 18–21). Similarly, hepatic glucose production will be increased in type 1 diabetes, if the disease is not properly controlled by insulin treatment.

Since existing forms of therapy of diabetes does not lead to sufficient glycaemic control and therefore are unsatisfying, there is a great demand for novel therapeutic approaches. Since the liver in diabetes is known to have an increased glucose production, compounds inhibiting this activity are highly desirable.

Recently, patents on inhibitors of the liver specific enzyme, glucose-6-phosphatase, which is necessary for the release of glucose from the liver, have been filed, for example German *Offenlegungsschrift* Nos. 4,202,183 and 4,202,184 and Japanese patent application No. 4-58565. All these known compounds are benzene derivatives.

International patent application having publication No. WO 92/16640 relates to di-, tri- and tetrasaccharides that are substrates or inhibitors of glycosyltransferase and glycosidase enzymes. Some specific compounds mentioned therein are 2,3,4,5-tetrahydroxypiperidine, 3,4,5-trihydroxy-6-methylpiperidin and 3,4-dihydroxy-5-methylpiperidine.

International Patent Application No. WO 92/21657 relates to certain ω-deoxyazapyranoses, e.g. 3,4-dihydroxy-5-methylpiperidine mentioned in claim 16 thereof. It is stated that these compounds have glucosidase inhibiting properties.

European patent application having publication No. 528,495 A1 relates to a class of azacyclic compounds, i.e. compounds comprising an azacyclic ring system substituted by arylmethyloxy or an arylmethylthio moiety. These compunds may be useful as tachykinin antagonists.

European patent application having publication No. 375,651 A1 relates to 1,4-dideoxy-1,4-imino-L-allitol and derivatives thereof having glycosidase inhibitory activity.

European patent No. 947 B2 relates to derivatives of 3,4,5-trihydroxypiperidine having α-glucosidase inhibitory activity which can be used for the treatment of diabetes.

European patent No. 22,192 B1 relates to 1-alkadien-2,4-yl-2-hydroxymethyl-3,4,5-trihydroxypiperidines having maximal action on α-glucosidase hydrolases and lipid absorption which can be used for the treatment of diabetes.

European patent application having publication No. 481,950 A2 relates to 3-fluoro analogs of 2-hydroxymethyl-4,5-dihydroxypiperidines having glycosidase inhibition activity.

In J.Am.Chem.Soc. 113 (1991), 6678, 3,4-dihydroxypiperidine, 3,4-dihydroxy-5-methylpiperidine and 3,4-dihydroxy-6-methylpiperidine are described as new compounds.

In J.Cell.Biochem., 1994, Suppl. 18D, 194 (published on Mar. 9, 1994) some catalytic antibodies, e.g. (3R,4R,5R)-3,4-di-hydroxy-5-hydroxymethylpiperidine hydrochloride and methyl 6,7-dideoxy-7-((3R,4R,5R)-3,4-dihydroxy-5-hydroxymethylpiperidinyl)-α-D-glucoheptopyranoside hydrochloride, are described.

In Dansk Kemi 74 (1993), 31, it is mentioned that Ms. Jespersen is making a report (dissertation) concerning synthesis of (3R,4R,5R)-3,4-dihydroxy-5-hydroxymethylpiperidine and it is stated therein that, possibly, this report is available. In this report, it is stated that this compound is a potential glycosidase inhibitor. Also in this report, 3-benzyloxy-4-hydroxy-5-hydroxymethylpiperidine is mentioned as an intermediate.

Moreover, scientifically it is well realized that inhibition of glycogen phosphorylase is a suitable target for the treatment of diabetes (Martin et al., 1991; Biochemistry 30: 10101–16; Oikonomakos et al., 1994; Eur. J. Drug Metab. Pharmakokin. 3: 185–92). These groups have used glucose analogs.

One object of the present invention is to furnish compounds which can be used as medicaments.

A further object of this invention is to furnish compounds which can effectively be used in the treatment of diabetes.

A still further object of this invention is to furnish compounds which can effectively be used as inhibitors of glucose production from the liver.

BRIEF DESCRIPTION OF THIS INVENTION

Surprisingly, it has been forund that compounds of the general formulas I and II stated in the claims, below, have interesting pharmacological properties. For example, the compounds of this invention can be used in the treatment of diabetes. Especially, the compounds of this invention are active as inhibitors of glucose production from the liver. Consequently, the compounds of this invention can be used for the treatment of the increased plasma glucose levels in diabetics.

DETAILED DESCRIPTION OF THIS INVENTION

Hereinafter, the term alkyl, when used alone or in combination with another moiety, is a straight or branched alkyl group which preferably contains not more than 8 carbon atoms, more preferred not more than 4 carbon atoms. Especially preferred alkyl groups are methyl, ethyl, propyl and isopropyl.

Preferably, hydroxyalkyl is hydroxymethyl or hydroxyethyl. Preferably, alkoxy is methoxy or ethoxy. Preferably, halogen is chloro, bromo or fluoro. Preferably, alkylamino is methylamino. Preferably, acylamino is alkylcarbonylamino, more preferred acetylamino. Preferably, dialkylamino is N,N-dimethylamino. Preferably, carboxyalkyl is methoxycarbonyl. Preferably, alkylthio is methylthio or ethylthio. Preferably, alkenyl is ethenyl or propenyl. Preferably, alkylphenyl is o-, m- or p-tolyl.

When the term trialkyl ammonium ion is used herein without stating which ion it is connected to, it is to be understood that it is connected to an ion, preferably the residue of an acid from which, for example, a hydrogen atom has been removed. Similar considerations apply for the terms quaternary ammonium base ion and N,N,N-trialkylammonium ion.

The term monosaccharide moiety designates a monosaccharide from which a hydrogen atom has been removed. Examples of preferred monosaccharides usable to form such moities ($R^1$) are glucose, fructose, galactose, mannose and methyl 6,7-dideoxy-D-gluco-hepto-pyranoside.

Examples of preferred compounds of formula I and II are (3R,4R,5R)-3,4-dihydroxy-5-hydroxymethylpiperidine, 3,4-dihydroxy-5-hydroxymethylpiperidine, 3-benzyloxy-4-hydroxy-5-hydroxymethylpiperidine, 3,4-dihydroxy-5-hydroxymethylpiperidineN-(7-(methyl 6,7-dideoxy-D-gluco-heptopyranoside)), 3,4-dihydroxy-5-methylpiperidine, 3,4-dihydroxy-5-ethylpiperidine, 3,4-dihydroxy-5-propylpiperidine, 3,4-dihydroxy-5-isopropylpiperidine, 3,4-dihydroxy-5-phenylpiperidine, 3,4-dihydroxy-5-hydroxyethylpiperidine, 3,4-dihydroxy-5-fluoromethylpiperidine, 3,4-dihydroxy-5-chloromethylpiperidine, 3-hydroxy-5-hydroxymethylpiperidine, 3-hydroxy-4-fluoro-5-hydroxymethylpiperidine, 3-hydroxy-4-chloro-5-hydroxymethylpiperidine, 3-fluoro-4-hydroxy-5-hydroxymethylpiperidine, 3-chloro-4-hydroxy-5-hydroxymethylpiperidine, 4-hydroxy-5-hydroxymethylpiperidine, N-methyl-3,4-dihydroxy-5-hydroxymethylpiperidine, N,N-dimethyl-3,4-dihydroxy-5-hydroxymethylpiperidinium chloride, (3R,4R)-3-hydroxy-4-hydroxymethylpyrrolidine, 3-hydroxy-4-hydroxymethylpyrrolidine, 3-benzyloxy-4-hydroxymethylpyrrolidine, 3-hydroxy-4-hydroxymethylpyrrolidine N-(7-(methyl 6,7-dideoxy-D-gluco-heptopyranoside)), 3-hydroxy-4-methylpyrrolidine, 3-hydroxy-4-ethylpyrrolidine, 3-hydroxy-4-propylpyrrolidine, 3-hydroxy-4-isopropylpyrrolidine, 3-hydroxy-4-phenylpyrrolidine, 3-hydroxy-4-hydroxyethylpyrrolidine, 3-hydroxy-4-fluoromethylpyrrolidine, 3-hydroxy-4-chloromethylpyrrolidine, 3-hydroxy-4-hydroxymethylpyrrolidine, 3-hydroxy-4-hydroxymethylpyrrolidine, 3-fluoro-4-hydroxymethylpyrrolidine, 3-chloro-4-hydroxymethylpyrrolidine, N-methyl-3-hydroxy-4-hydroxymethylpyrrolidine and N,N-dimethyl-3-hydroxy-4-hydroxymethylpyrrolidinium chloride.

The compounds of formulas I and II may be presented as a mixture of enantiomers which, if desired, may be resolved into the individual pure enantiomers. This resolution may conveniently be performed by fractional crystallization from various solvents, of the salts of compounds of the formula I or II with optical active acids or by other methods known per se, for example, chiral column chromatography. This invention includes all isomers, whether resolved or mixtures thereof.

Examples of pharmaceutically acceptable salts are acid addition salts with non-toxic acids, either inorganic acids such as hydrochloric acid, sulphuric acid and phosphoric acid, or organic acids such as formic acid, acetic acid, propionic acid, succinic acid, gluconic acid, lactic acid, citric acid, ascorbic acid, benzoic acid, embonic acid, methanesulphonic acid and malonic acid.

The compounds of formulas I and II are prepared by methods known per se by the skilled art worker, for example as described in the following. One synthetic strategy can be to employ a chiral Cerny epoxide (Tanka, T. and Cerny, M. *Collection Czechoslov. Chem. Commun:* 36 (1971), 2216), which is opened by a reagent to introduce a hydroxymethyl group (as illustrated in Example 1, below) or another alkyl or substituted alkyl substituent. After hydrolysis of the anhydro bond, the pentodialdose could be obtained by oxidative cleavage of the carbon chain. As illustrated in Example 1, (3R,4R,5R)-3,4-dihydroxy-5-hydroxymethylpiperidine was prepared by reductive amination of the pentodialdose. Similarly, other compounds of the general formula I or II can be prepared by the above strategy. A variety of functional groups can be introduced in the compounds prepared as outlined above by methods well known to those skilled in the art.

Pharmaceutical Compositions

This invention further provides pharmaceutical compositions which comprise at least one compound of formula I or II or a pharmaceutically acceptable salt thereof in connection with a pharmaceutically acceptable carrier. Such compositions may be in the form of powders, solutions, or suspensions, which may or may not be divided in unit dosage form or in the form of capsules or tablets.

The pharmaceutical compositions of this invention may comprise carriers, diluents, absorption enhancers, tablet disintegrating agents and other ingredients which are conventionally used in the art. The powders and tablets preferably contain from 5 to 99%, more preferred from 10 to 90% of the active ingredient. Examples of solid carriers are magnesium carbonate, magnesium stearate, dextrin, lactose, sugar, talc, gelatin, pectin, tragacanth, methyl cellulose, sodium carboxymethyl cellulose, low melting waxes and cocoa butter.

Liquid compositions include sterile solutions, suspensions and emulsions suitable for parenteral injection.

The route of administration of the compositions containing a compound of formula I or II may be any route which effectively transports the active compound to its site of action, the oral or nasal route being preferred.

The regimen for any patient to be treated with the compositions according to the present invention should be determined by those skilled in the art. The daily dose to be administered in therapy can be determined by a physician and will depend on the particular compound employed, on the route of administration and on the age and the condition of the patient. A convenient daily dosage can be less than about 1 g, preferably in the range around 10–200 mg.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

EXAMPLE 1

Synthesis of (3R,4R,5R)-3,4-dihydroxy-5-Hydroxymethylpiperidine

The title compound was synthesized by a 6 step procedure starting from 1,6:2,3-dianhydro-4-O-benzyl-β-D-mannopyranose as outlined below:

1,6-Anhydro-4-O-benzyl-2-deoxy-2-C-vinyl-β-D-glucopyranose:

To a stirred solution of 1,6:2,3-dianhydro-4-O-benzyl-β-Dmannopyranose (prepared as outlined by Tanka, T. and Cerny, M. *Collection Czechoslov. Chem. Commun:* 36 (1971), 2216) (5.0 g, 21.3 mmol) in dry tetrahydrofurane (hereinafter designated THF) (25 ml), was added a solution of 1.77M vinylmagnesiumbromide in THF (120.5 ml, 213 mmol). The mixture was gently refluxed for 3 h at 60° C. After cooling to room temperature, a 2M $NH_4Cl$ aqueous solution (650 ml, pH value: 8) was slowly added. The aqueous layer was extracted with ethyl acetate (2×250 ml). The combined organic layers were dried ($MgSO_4$), filtered and concentrated. The crude product (4.87 g, 87%) was purified by flash chromatography using ethyl acetate/pentane (1:2) as eluent, to give 1,6-anhydro-4-O-benzyl-2-deoxy-2-C-vinyl-β-D-glucopyranose as a white crystalline compound in 75.5% (4.23 g) yield. After recrystallization in ethanol, the melting point was 88°–91° C. 13C-NMR (50 MHz, $CDCl_3$): δ135.5 (CH=); 137.7, 128.3, 127.6, 127.5 (phenyl, hereinafter designated Ph); 117.2 ($CH_2$=); 103.5 (C-1); 78.8 (C-4); 74.6 (C-3); 71.3, 70.4 (C-5, $OCH_2Ph$); 65.4 (C-6); 51.8 ppm (C-2). 1H NMR (200 MHz, $CDCl_3$): d 7.35 (d, 5H, Ph); 5.99 (m, 1H, CH=$CH_2$); 5.25 and 5.17 (s, 1H and d, 1H, $CH_2$=); 4.63 (dd, 3H, $OCH_2Ph$ and H-5); 4.09 and 3.75 (d, 1H og m, 2H, H-3, H-6 og H-6'); 3.43 (s, 1H, H-4); 2.80 (broad s, 1H, OH); 2.45 (d, 1H, H-2). Analytical calculation for $C_{15}H_{18}O_4$: C: 68.69; H: 6.92. Found: C: 68.58; H: 6.94.

1,6-Anhydro-4-O-benzyl-2-deoxy-2-C-hydroxymethyl-β-D-glucopyranose:

A stream of ozone (0.36 mmol/minute) was passed through a solution of 1,6-anhydro-4-O-benzyl-2-deoxy-2-C-vinyl-β-Dgluco-pyranose, (3.36 g, 12.8 mmol) in ethanol (100 ml) for 43.5 minutes. The solution of the ozonide was transfered to a three necked round bottomed flash equiped with thermometer and a dropping funnel containing a solution of $NaBH_4$ (3.87 g, 102 mmol) in ethanol/water (1:1; 35 ml). The solution of $NaBH_4$ was added dropwise in such a manner to keep the temperature below 20° C. (cooling on ice bath). After stirring for 45 minutes, Amberlite IR 120, $H^+$(100 ml) was added. After stirring for another 30 minutes, the ion exchange resin was filtered off and rinsed with water. The solution was evaporated and co-concentrated with methanol (3×80 ml). The residue was a colourless sirup in 96% (3.28 g) yield. This sirup was flash chromatographed using ethyl acetate/pentane (2:1) and ethyl acetate as eluent to give the title compound in a 63% (2.14 g) yield as a crystalline compound. In some runs, the crude sirup crystallised and was recrystallised from chloroform:

melting point 111°–113° C. 13C-NMR (50 MHz, $D_2O$): d 139, 130.1, 129.8 (Ph); 102.0 (C-1); 80.5 (C-4); 76.1 (C-3); 72.9 ($OCH_2Ph$); 67.4 (C-5); 66.2 (C-6); 61.7 (C-2'); 49.0 ppm (C-2). Analytical calculation for $C_{14}H_{18}O_5$: C: 63.15; H: 6.81. Found: C: 63.14; H: 6.79.

4-O-Benzyl-2-deoxy-2-C-hydroxymethyl-D-glucopyranose:

1,6-Anhydro-4-O-benzyl-2-deoxy-2-C-hydroxymethyl-β-D-gluco-pyranose (1.59 g, 6.0 mmol) was dissolved in 1M sulfuric acid (30 ml) by heating to reflux. The anhydride was refluxed for 1 hour. After cooling to room temperature, the solution was poured through a column containing Amberlite® IR 67, $OH^-$(120 ml). The column was rinsed with water followed by methanol (400 ml). The eluated liquid was concentrated. The residue was a colourless sirup obtained in 98% (1.67 g) yield. Flash chromatography using ethyl acetate and ethyl acetate/methanol (10:1) as eluent gave the product in 76% (1.29 g) yield. One of the anomers (β) could be obtained by crystallization in ethyl acetate in 27% yield as a white crystalline compound. Melting point:, 102°–105° C. 13C-NMR (50 MHz, $D_2O$): d 136.8, 128.3, 128.0 (Ph); 94.1 (C-1, β); 91.4 (C-1, α); 78.6 (C-4); 74.4 (C-3); 70.3 ($OCH_2Ph$, C-6 β); 69.5 (C-6, α); 60.3 (C-5); 59.1 (C-2', α); 56.6 (C-2', β); 47.7 ppm (C-2, α). 1H-NMR (200 MHz, $D_2O$); 5.13 (d, 1H, H-1 (α), $J_{1,2}$=3.5 Hz); 4.48 (d, 1H, H-1 (β), $J_{1,2}$=10 Hz). Analytical calculation for $C_{14}H_{20}O_6 \times 0.3 H_2O$: C: 58.04; H: 7.17. Found: C: 58.07; H: 7.19.

4-O-Benzyl-2-deoxy-2-C-hydroxymethyl-D-xylo-pentodialdose:

To a solution of 4-O-benzyl-2-deoxy-2-C-hydroxymethyl-D-gluco-pyranose (1.41 g, 5.0 mmol) in methanol (15 ml), a solution of sodium periodate (5.35 g, 25.0 mmol) in water (50 ml) was added dropwise over 15 minutes. Further, methanol (25 ml) was added. The mixture was stirred at 45° C. for 3 hours. The precipitated iodate was filtered off, and the mixture was concentrated. By resolution of the residue in ethyl acetate/ethanol (1:1; 80 ml), more iodate was precipitated and filtered off. The mother liquour was concentrated and the residue (2.07 g) was flash chromatographed using ethyl acetate as eluent. The purified product was obtained as a yellow sirup in 87% (1.09 g) yield and 9% of unreacted starting material (0.13 g) was isolated. The purified product was used imidiately in the next reaction.

(3R,4R,5R)-3-Benzyloxy-4-hydroxy-5-hydroxymethylpiperidine:

To a solution of 4-O-benzyl-2-deoxy-2-C-hydroxymethyl-D-xylo-pentodialdose (1.77 g) in ethanol (40 ml), 0.29M $NH_3$ in ethanol (162 ml) and 5% palladium on charcoal (300 mg) was added. The mixture was hydrogenated at 500 Psi at 20° C. for 15 hours. The reaction mixture was filtrated and concentrated. The residue (1.85 g) was flash chromatographed using ethanol/$NH_4OH$ (25% aqueous)/trimethylamine (122:2:1) as eluent giving the product as a colourless sirup (getting coloured after storing) in 78% yield. 13C-NMR (62.9 MHz, $D_2O$): δ138.1, 128.1, 127.3 (Ph); 80.6 (C-3), 74.9 (C-4); 71.8 ($OCH_2Ph$); 62.5

(C-5'); 48.0 (C-2); 46.8 (C-6); 45.0 ppm (C-5). 1H-NMR (500 MHz, D$_2$O): δ7.3 (s, 5H, Ph); 4.65, 4.51 (2 d, 2H, OCH$_2$Ph, J$_{gem}$=12 Hz); 3.66 (dd, 1H, H-5a', J$_{5a',5b'}$=10 Hz, J$_{5',5}$=5.5); 3.57 (dd, 1H, H-5'b, J$_{5a'}$,5b'=10 Hz, J$_{5b',5}$=4.5); 3.41 (dd, 1H, H-4, J$_{3,4}$=11 Hz, J$_{4,5}$=9 Hz); 3.3 (broad, N—H); 3.27 (dd, 1H, H-3, J$_{3,2ax}$=11 Hz, J$_{3,2eq}$=4 Hz); 3.22 (dd, 1H, H-2eq, J$_{2eq,2ax}$=11, J$_{2eq,3}$=4 Hz); 2.97 (dd, 1H, H-6 eq, J$_{6eq,6ax}$=12 Hz, J$_{6eq,5}$=4 Hz); 2.38 (t, 1H, H-2ax, J$_{2ax, 2eq}$=J2ax,3=11 Hz); 2.31 (t, 1H, H-6ax, J$_{6ax,6eq}$=J6ax,5=12 Hz); 1.80 ppm (m, 1H, H-5).

(3R,4R,5R)-3,4-Dihydroxy-5-hydroxymethylpiperidine hydrochloride:

(3R,4R,5R)-3-Benzyloxy-4-hydroxy-5-hydroxymethylpiperidine (0.527 g, 2.2. mmol) was dissolved in 0.5M HCl (5.3 ml) and ethanol (50 ml) and 5% palladium charcoal (300 mg) was added. The mixture was hydrogenated at 101 kPa and 20° C. for 18 hours. The reaction mixture was filtrated and concentrated to give the product in 93% (0.375 g) yield. 13C-NMR (50 MHz, D$_2$O): d 70.7 og 68.1 (C-3 og C-4); 58.6 (C-5'); 46.2 og 44.4 (C-2 og C-6); 40.6 (C-5). 1H-NMR (500 MHz, D$_2$O, Ph<1, ref. 4.63 ppm): d 3.72 (dd, 1H, H-5b',J$_{5a',5b'}$=11.5, J$_{5,5b'}$=3.3 Hz); 3.67 (ddd, 1H, H-3, J$_{3,2ax}$=11.2, J$_{3,4}$=8.9,J$_{3,2eq}$=4.9 Hz); 3.64 (dd, 1H, H-5a', J$_5$a',5b'=11.5,J$_{5a',5}$=6.2 Hz); 3.43 (ddd, 1H, H-2eq, J$_{2eq,2ax}$=12.7, J$_{2eq,3}$=4.9, J$_{2eq,6eq}$=2.0); 3.42 (dd, 1H, H-4, J$_{4,5}$=10.5, J$_{4,3}$=8.9 (Hz); 3.41 (ddd, 1H, H-6eq, J$_{6eq, 6ax}$=13.4, J$_{6eq,5}$=3.8, J$_{6eq,2eq}$=2.0 Hz); 2.87, 12.7, J$_{2ax,3}$=11.2 Hz); 1.86 ppm (ddddd, 1H, H-5). If necessary, the piperidine could be chromatographed using ethanol/NH4OH (25% aqueous) (10:1) to give the free piperidine. Analytical calculation for C$_6$H$_{13}$NO$_3$: C: 48.97; H: 8.90; N: 9.52. Found: C: 48.46; H: 9.33; N: 9.17.

EXAMPLE 2

Experimental Protocol and Results

Rat hepatocytes were isolated using a standard two step collagenase technique, and cultured onto collagen coated culture dishes for 72 hours in medium 199 with the addition of dexamethazone (0.1 μM); penicillin/Streptomycin ((100 u/100 μg)/ml) and insulin (1 nM). During the last 24 hours, the hepatocytes were cultured in the presence of high levels of insulin (5 nM) and glucose (15 mM), which result in the incorporation of glucose into glycogen. Therefore, at the time of the experiment, the cells mimic livers from fed animals.

Experiments were initiated after 72 hours of culture by 2 times wash of cells and addition of a 20 mM HEPES experimental buffer including balanced salts, but without glucose. The test compound was added simultaneously with the experimental buffer. To some cultures, glucagon (0.5 nM) was added after 10 minutes in order to stimulate glucose production from liver cells. The glucose released into the media, reflecting the glucose production of the liver cells, was measured 70 minutes after the start of the experiment and standardized to cellular DNA content.

Phosphorylase was either purchased from Sigma or extracted from rat livers according to Stalmans et. al. (Eur. J. Biochem. 49 (1974), 415). The activity of phosphorylase was determined as described by Bergmeyer (1983; in : Meth. of Enzymatic Analysis, 2 pp 293–295, Weinheim, (ed.) Verlag Chemie).

The activity of the glycogen debranching enzyme, α-1, 6-glucosidase was determined as described by Brown and Brown (1966; in : Meth. in Enzymology, 8 : 515–524, Neufeld and Ginsburg (Eds.) Academic Press).

Table 1 below shows the results obtained with the compound of example 1 on basal and glucagon stimulated glycogenolysis. The effects are compared to those exerted by the model debranching enzyme inhibitor 1-deoxynojirimycin (hereinafter designated dNOJ).

TABLE 1

Effects of Example 1 on baseline and glucagon stimulated glucose production from cultured liver cells. Values are expressed relative to the basal glucose production. Results obtained with the model α-1,6 glucosidase inhibitor 1-deoxynojirimycin are shown for comparison.

| | Glucose production | |
|---|---|---|
| | Without glucagon | With glucagon (0.5 nM) |
| No addition: | 100% | 283% |
| Example 1 (32 μM): | 17% | 32% |
| 1-deoxynojirimycin (50 μM): | 89% | 237% |

The results clearly demostrate the ability of the compound of example 1 to inhibit basal and glucagon stimulated hepatocyte glucose production, while dNOJ only exerted marginal effects.

Table 2 compares the potency of the compound of example 1 with the potency of dNOJ on various cellular and enzymatic activities.

TABLE 2

Effects of compound of example 1 compared to effects of 1-deoxynojirimycin on different cellular and enzymatic activities. The results are the concentrations of the compounds resulting in half maximal activity (I.C.$_{50}$).

| | I.C.$_{50}$ values (μmoles/L) | |
|---|---|---|
| | Example 1 | 1-deoxynojirimycin |
| Liver cell glucose production: | | |
| Basal: | 1.3 | >100 |
| Glucagon stimulated: | 1.6 | >100 |
| Phosphorylase: | 1.12 | >200 |
| liver α-1,6-glucosidase | 77 | 2.4 |
| Ycast α-1,6-glucosidase* | 85.9 | 25.4 |

*From: Jespersen et al. (Angew. Chem. Int. Ed. Engl. 33 (1994), 1778)

It is apparent from the presented data in table 2 that the compound of example 1 is a potent inhibitor of liver cell glucose production. Moreover, it is also demonstrated that phosphorylase is inhibited by this compound in similar low concentrations. In contrast, the compound of example 1 is only a very weak inhibitor of α-1,6-glucosidase either from liver or from yeast.

Table 2 also demonstrates that the potent model inhibitor of liver α-1,6-glucosidase was unable to inhibit either liver cell glucose production or phosphorylase. These data are in agreement with data obtained by Bollen and Stalmans (Eur. J. Biochem. 181 (1980), 775), who also concluded that α-1,6-glucosidase inhibition is an insufficient principle for inhibition of liver cell glucose production.

In conclusion, the data demonstrates that inhibition of liver cell glucose production by the compounds of formula I and II according to this invention, as examplified by the compound of example 1, is mediated by inhibition of phosphorylase. Consequently, the compounds of formula I and II can be used to inhibit both the base line and glucagon stimulated glucose production from liver cells.

EXAMPLE 3

Tablets

Tablets which are suitable for oral administration and which contain the below-mentioned components are produced in a manner known per se granulating the active and the auxiliary substances and making them into tablets.

Each tablet contains 50 mg of the compound of formula I or II, e.g. the compound of Example 1, 100 mg of lactose, 30 mg of corn starch, 3 mg of talc powder, 3 mg of colloidal silicon dioxide and 2 mg of magnesium stearate.

EXAMPLE 4

Capsules

Capsules which are suitable for oral administration contain the below-mentioned components are produced in a manner known per se mixing the active substances with the auxiliary substances and putting them into gelatine capsules.

Each capsule contains 50 mg of the compound of formula I or II, e.g. the compound of example 1, 100 mg of lactose, 30 mg of corn starch, 3 mg of talc powder, 3 mg of colloidal silicon dioxide and 2 mg of magnesium stearate.

We claim:

1. A pharmaceutical composition comprising a compound of formula I

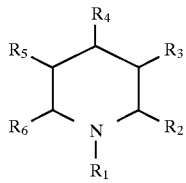

wherein

R$^1$ represents hydrogen, a monosaccharide moity or alkyl which optionally is substituted by one or more of the following groups: hydroxy, hydroxyalkyl, halogen, amino, alkylamino, dialkylamino, a trialkylammonium ion, nitro, formyl, carboxy, carboxyalkyl, alkylthio, alkenyl, phenyl and alkylphenyl, or R1 together with the adjacent nitrogen atom from the piperidine nucleus represents a quaternary ammonium base ion residue containing two alkyl groups which optionally are substituted by one or more of the following groups: hydroxy, hydroxyalkyl, halogen, amino, alkylamino, dialkylamino, a trialkylammonium ion, nitro, formyl, carboxy, carboxyalkyl, alkylthio, alkenyl, phenyl and alkylphenyl;

R2, R3, R4 and R6, which are the same or different, independent of each other represents hydrogen, hydroxy, hydroxyalkyl, halogen, amino, alkylamino, acylamino, N,N-dialkylamino, a N,N,N-trialkylammonium ion, nitro, formyl, carboxy, benzoxy, mercapto, alkylthio, alkenyl, phenyl and alkylphenyl; and R5 represents phenyl or methyl which optionally is substituted by one or more of the following groups: alkyl, hydroxy, hydroxyalkyl, halogen, amino, alkylamino, dialkylamino, trialkylammonium, nitro, formyl, carboxy, carboxyalkyl, alkylthio, alkenyl, phenyl and alkylphenyl; with the proviso that said compound contains at least 2 free or protected hydroxy groups; or a pharmaceutically acceptable salt thereof and a pharmaceutically acceptable carrier.

2. The pharmaceutical composition of claim 1, wherein the compound is (3R,4R,5R)-3,4-dihydroxy-5-hydroxymethylpiperidine.

3. The pharmaceutical composition of claim 1, wherein the compound is 3-benzyloxy-4-hydroxy-5-hydroxymethylpiperidine.

4. A pharmaceutical composition comprising a compound of formula II

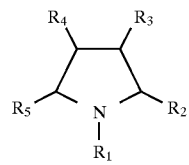

wherein

R$^1$ represents hydrogen, a monosaccharide moiety or alkyl which optionally is substituted by one or more of the following groups: hydroxy, hydroxyalkyl, halogen, amino, alkylamino, dialkylamino, a trialkylammonium ion, nitro, formyl, carboxy, carboxyalkyl, alkylthio, alkenyl, phenyl and alkylphenyl, or R1 together with the adjacent nitrogen atom from the pyrrolidine nucleus represents a quaternary ammonium base ion residue containing two alkyl groups which optionally are substituted by one or more of the following groups: hydroxy, hydroxyalkyl, halogen, amino, alkylamino, dialkylamino, a trialkylammonium ion, nitro, formyl, carboxy, carboxyalkyl, alkylthio, alkenyl, phenyl and alkylphenyl;

R2, R3 and R5, which are the same or different, independent of each other represents hydrogen, hydroxy, hydroxyalkyl, halogen, amino, alkylamino, N,N-dialkylamino, a N,N,N-trialkylammonium ion, nitro, formyl, carboxy, benzoxy, mercapto, alkylthio, alkenyl, phenyl and alkylphenyl; and R4 represents carboxy, phenyl or methyl which optionally is substituted by one or more of the following groups: alkyl, hydroxy, hydroxyalkyl, halogen amino, alkylamino, dialkylamino, a trialkylammonium ion, nitro, formyl, carboxy, carboxyalkyl, alkylthio, alkenyl, phenyl and alkylphenyl, or R1 together with the adjacent nitrogen atom from the pyrrolidine nucleus represents a quaternary ammonium base ion residue containing two alkyl groups which optionally are substututed by one or more of the following groups: hydroxy, hydroxyalkyl, halogen, amino, alkylamino, dialkylamino, a trialkylammonium ion, nitro, formyl, carboxy, carboxyalkyl, alkylthio, alkenyl, phenyl and alkylphenyl;

R2, R3, R4, R5, which are the same or different, independent of each other represents hydrogen, hydroxy, hydroxyalkyl, halogen, amino, alkylamino, N,N-dialkylamino, a N,N,N-trialkylammonium ion, nitro, formyl, carboxy, benzoxy, mercapto, alkylthio, alkenyl, phenyl; and R4 represents carboxy, phenyl or methyl which optionally is substituted by one or more of the following groups: alkyl, hydroxy, hydroxyalkyl, halogen, amino, alkylamino, dialkylamino, a trialkylammonium ion, nitro, formyl, carboxy, carboxyalkyl, alkylthio, alkenyl, phenyl and alkylphenyl; with the proviso that said compound contains at least 2 free or protected hydroxy groups; or a pharmaceutically acceptable salt thereof and a pharmaceutically acceptable carrier.

5. A method of treating diabetes which method comprises administering an effective amount of the pharmaceutical composition according to claim 1 to a patient in need of such a treatment.

6. A method of inhibiting the liver glucose production from the liver, comprising administering an effective amount of the pharmaceutical composition according to claim 1 to a patient in need of such a treatment.

7. A method of treating diabetes which method comprises administering an effective amount of the pharmaceutical composition according to claim 4 to a patient in need of such a treatment.

8. A method of inhibiting the liver glucose production from the liver, comprising administering an effective amount of the pharmaceutical composition according to claim 4 to a patient in need of such a treatment.

* * * * *